(12) United States Patent
Eichenlaub et al.

(10) Patent No.: US 6,544,796 B1
(45) Date of Patent: Apr. 8, 2003

(54) SYSTEM FOR PRODUCING MULTIPLE DIAGNOSTIC TEST ELEMENTS

(75) Inventors: Udo Eichenlaub, Habach (DE); Martin Masch, Munich (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/380,070

(22) PCT Filed: Feb. 23, 1998

(86) PCT No.: PCT/EP98/01022

§ 371 (c)(1),
(2), (4) Date: Mar. 31, 2000

(87) PCT Pub. No.: WO98/36833

PCT Pub. Date: Aug. 27, 1998

(30) Foreign Application Priority Data

Feb. 24, 1997 (DE) .......................................... 197 07 204

(51) Int. Cl.⁷ .............................................. G01N 21/75
(52) U.S. Cl. .................. 436/166; 436/808; 422/58; 422/61; 427/258; 427/286; 427/338; 427/414
(58) Field of Search ............................... 422/56–58, 61; 427/258, 286, 338, 414; 436/164, 165, 180, 807–810

(56) References Cited

U.S. PATENT DOCUMENTS

| | | |
|---|---|---|
| 4,046,513 A | 9/1977 | Johnson |
| 4,216,245 A | 8/1980 | Johnson .......................... 427/2 |
| 4,496,654 A | 1/1985 | Katz et al. ...................... 435/7 |
| 4,591,570 A | 5/1986 | Chang .......................... 436/518 |
| 4,664,885 A | 5/1987 | Minekane et al. ............. 422/65 |
| 5,338,688 A | 8/1994 | Deeg et al. ................. 436/180 |
| 5,378,638 A | 1/1995 | Deeg et al. ................. 436/518 |
| 5,424,220 A | 6/1995 | Goerlach-Graw et al. .. 436/568 |

FOREIGN PATENT DOCUMENTS

| | | |
|---|---|---|
| DE | 2727347 C2 | 12/1977 |
| DE | 2818826 A1 | 11/1978 |
| EP | 0119573 A1 | 9/1984 |
| EP | 0268237 A3 | 5/1988 |
| EP | 0353592 A2 | 2/1990 |
| GB | 1526708 | 9/1978 |
| GB | 1601283 | 10/1981 |
| JP | 1036449 | 2/1989 |
| WO | WO 89/10192 | 11/1989 |
| WO | WO 95/35505 | 12/1995 |
| WO | WO 97/44134 | 11/1997 |

OTHER PUBLICATIONS

Kimura, J., et al., "An Immobilized Enzyme Membrane Fabrication Method using an Ink Jet Nozzle" Biosensors 4 (1988) 41–52.

*Primary Examiner*—Lyle A. Alexander
(74) *Attorney, Agent, or Firm*—Brinks Hofer Gilson & Lione

(57) ABSTRACT

A system for producing multiple diagnostic test elements has a support (1) with an analytical region (3) to which diagnostic test spots (8) are applied, one or several stop edges (11–13) for each direction in space for positioning the support, a first holding unit (10I) into which the support is inserted and positioned by means of the one or more stop edges, a first printing head (20I) arranged above the holding unit (10) for applying drops of a first liquid to the analytical region of the support (1), a first positioning unit which laterally displaces and positions the first holding unit, a second holding unit (10II) into which the support is inserted and positioned by means of the one or more stop edges, a second printing head (20II) arranged above the second holding unit for applying drops of a second liquid to the analytical region of the support (1), a second positioning unit which laterally displaces and positions the second holding unit, a transport unit (41) and a control unit.

31 Claims, 9 Drawing Sheets

SYSTEM FOR PRODUCING MULTIPLE DIAGNOSTIC TEST ELEMENTS

Figure 1:
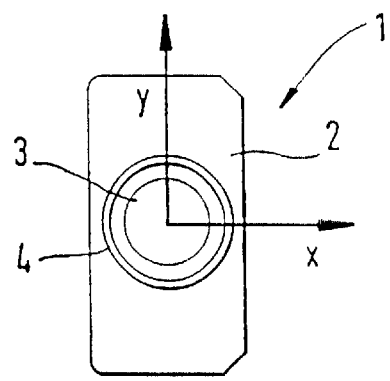

The present invention concerns a system for producing multiple diagnostic test elements comprising,
- a support with an analytical region for applying diagnostic test spots and one or several stop edges for each direction in space to position the support,
- a first holding unit into which the support is inserted and positioned by means of one or several stop edges,
- a first printing head which is arranged above the holding unit and which is used to release fluid drops of a first liquid onto the analytical region of the support,
- a first positioning unit which laterally displaces and positions the first holding unit,
- a second holding unit into which the support is inserted and positioned by means of one or several stop edges,
- a second printing head which is arranged above the second holding unit and is used to release fluid drops of a second liquid onto the analytical region of the support,
- a second positioning unit which laterally displaces and positions the second holding unit,
- a transport unit which transports the support into the holding units,
- a control unit which controls the transport unit, the holding units and the positioning units and the release of liquid from the printing heads.

The present invention additionally concerns multiple diagnostic test elements in which a plurality of test spots are arranged particularly exactly in a predetermined pattern and also a production process for such test elements and an analytical method using multiple test elements.

Test elements have already been known for some time in the prior art in which various reagents are applied to a support. For example an indicator is described in the German Patent DE 27 27 347 in which two or several substances are applied to zones on the support surface on a support which have a certain spacing. Printing techniques such as screen printing or electrostatic printing and the so-called ink-jet printing are disclosed for applying the reagents to the surface. A process for the production of reagent supports is also described in U.S. Pat. No. 4,216,245 in which two or several reagents are applied in non-overlapping regions of the surface. In the aforementioned documents this procedure is chosen to avoid undesired interactions of the reagents. In contrast test elements are described in the U.S. Pat. Nos. 5,378,638 and 4,591,570 that are suitable for immunological tests. A method is described in U.S. Pat. No. 4,591,570 in which various solutions of antibodies are applied manually to the support using a pipette. The diameter of the surface regions (spots) is between 0.25 and 1 mm. An apparatus for the automatic production of supports containing a plurality of small test spots is described in U.S. Pat. No. 5,338,688. The support to be coated is located on a positioning table which can be moved laterally and a single printing head for applying drops of liquid is located above the support. In this document it is pointed out that it is possible to generate patterns of various types of liquid which are arranged alternately. However, it is not shown how such a pattern can be generated in practice.

The object of the present invention was to propose a device and a process for the production of multiple test elements which produces test elements that have particularly small test zones in a highly accurate predetermined arrangement. In particular an object of the present invention was to provide such precise test elements in which the test spots have different compositions. An additional object of the present invention was to propose a device for producing test elements and a suitable process that can be used to reliably and rapidly produce the test elements according to the invention.

The present invention has achieved the said objects by providing a system as claimed in claim 1. This system can be used to produce multiple test elements which have a very accurate pattern of small test zones.

Multiple test elements which can be produced with a production system of the present invention have a support on which an analytical region is located. A plurality of essentially circular test spots is applied in the analytical region in a specified pattern. The diameter of the individual test spots is preferably less than 350 $\mu$m and the centres of the test spots deviate by less than 40 $\mu$m from the specified pattern. Such an accurate arrangement of test spots is unknown in the prior art. Letters and such like can also be generated by a pattern of very accurately arranged individual spots when using ink-jet printing heads in conventional printers. However, a problem in the present invention is that the test zones of the multiple test elements cannot be applied with a single printing head and instead several printing heads filled with different printing liquids are required. Colour printers are known in the prior art in which different liquids are applied using several printing heads or one printing head with several chambers. In such colour printers the paper and the printing heads are moved. Such an arrangement is less suitable for the production of very precise test elements since neither the absolute nor the relative accuracies of the positioning are adequate. In addition colour printers of the prior art do not enable the high printing densities required for the present invention composed of different test spots that are separated from one another. It was found that the positioning inaccuracy is mainly due to the fact that the printing heads are moved during the printing process. Other disadvantages of colour printers are the use of a relative large distance between the discharge nozzle of the printing head and the printed material. The present invention discloses an improved method and system for producing exact test elements with different test spots which avoids the disadvantages of the prior art.

In the production of multiple test elements the manufacture already knows the desired pattern so that a deviation of the test spots from the pattern and the extent of the deviation can be simply determined by a microscopic evaluation or similar methods. The deviation from the pattern can, however, also be determined when the specified pattern is unknown since the patterns used in practice are strict geometric arrangements such as squares, rectangles, honeycombs etc. In the said patterns there are always rows of test spots. Hence, in order to determine deviations from the pattern, the centres of test spots that are located in a row can be joined together by a fitting line. The deviation from the pattern is given in a simple manner by the distance of the individual test spot centres from the line of fit. In this definition of distance it is assumed that different types of test spots are in the observed rows. It is technically relatively simple to achieve the inventive precision for rows of similar test spots which can be produced with one and the same printing head.

The analytical region of multiple test elements according to the invention is preferably planar and has an unevenness of less than 100 $\mu$m, particularly preferably of less than 10 $\mu$m. The analytical region is preferably made of a material into which the liquids cannot penetrate or only to a very slight extent. Suitable materials are in particular plastics of which polystyrene has proven to be particularly advantageous. However, the analytical region can also be composed of glasses, metals or silicon which have suitable surface properties. The analytical region onto which the test spots are applied is preferably hydrophobic in order to avoid bleeding of the printed liquid drops. The use of a hydrophobic surface for the analytical region, compatible printing liquids to generate test spots and suitable methods for applying test spots can ensure that the test spots have a defined size and shape.

The analytical region should also have a sufficiently homogeneous surface which has only a few defects and little unevenness. The defects on the surface should be so small that the longest dimension of the imperfection is less than 10 μm and the unevenness of the surface should be preferably less than or equal to 10 μm.

A preferred use according to the invention of the multiple test elements is for analyses using fluorescent light. In this case it has proved to be advantageous to select materials at least for the analytical region and preferably for the entire support which on the one hand are not excited by fluorescent radiation to emit light and on the other hand do not reflect the fluorescent radiation that is used. Such materials can be obtained in a suitable manner by mixing plastics with carbon black.

Multiple test elements can be obtained according to the invention which have the shape of a strip or such like and are dipped into a sample solution or onto which the sample solution is applied. However, it has turned out that the multiple test elements according to the invention can be used particularly well for detection methods in which the test spots are incubated together with the sample. These are in particular immunological test methods in which an antigen-antibody reaction takes place. In order to carry out such an incubation with very small amounts of sample, the analytical region of the multiple test elements is surrounded by a rim such that the rim and analytical region together form a well. The sample liquid to be examined and optionally additional liquids such as reagents are added to this well. Such a multiple test element enables a plurality of analytical tests to be carried out using sample volumes of a few microlitres. The height of the said rim is adapted to the amount of liquid which is to be held by the well. The rim typically has a height of about 2 mm.

It has turned out that it is advantageous for the production of a multiple test element according to the invention and for carrying out analytical tests if the support of the test element has a basal surface which is parallel to the analytical region and serves to position the support vertically. In particular it is advantageous when the basal surface used for positioning is arranged on the same side of the support as the analytical region. In addition it has turned out according to the invention that the positioning is particularly exact and the production process is particularly optimal when the support is inserted from the underside into a holding unit in which the test spots are applied. Therefore the region of the basal surface used as a stop is preferably on the surface of the support where the analytical region is also located.

Furthermore it is advantageous for the production and use of the multiple test elements when one or several cross-pieces are mounted on the basal surface which run essentially perpendicular to the basal surface and provide the stop edges for two directions in space. For manufacturing reasons it has proven to be advantageous when the cross-pieces are located on the underside of the basal surface i.e. on the side of the support which faces away from the analytical region.

The cross-pieces serve to position the test elements in a plane (lateral positioning). It has proven to be advantageous when the test elements have pairs of cross-pieces which are opposite one another so that a lever for positioning can engage with one cross-piece of such a pair and the second cross-piece of the pair is pressed against a stop in a holding unit. In addition cross-pieces have proven to be advantageous which have a U shape in a top-view on the basal surface of the support. This type of cross-piece enables the multiple test elements according to the invention to be stacked and on the other hand they can be displaced horizontally in the stacked state if two U shaped cross-pieces are used with a spacing in between which is larger than the diameter of the well.

A system for producing multiple test elements has at least two holding units in which the supports or the multiple test elements can be inserted. The holding unit has several stop edges against which the stop edges of the supports are pressed. Usually three different types of stop edges are used. On the one hand the basal surface of the support is moved against one or several stop edges which position it in the vertical direction. The support is preferably inserted from below into the holding unit and the holding unit has stops against the underside of which the upper side of the support is positioned. In addition a holding unit has stop edges for the two lateral directions in space against which the support is positioned.

Printing heads are arranged above the holding units from which drops of liquid are applied to the analytical regions of the support. The printing heads for liquids described in U.S. Pat. No. 5,338,688 and EP-A-0 268 237 are for example suitable as printing heads. However, other printing heads known in the prior art are also suitable such as those used for ink-jet or bubble-jet printers. Since such printing heads are widely used a more detailed description is not given but rather reference is merely made to the complete contents of the already mentioned patent documents.

The invention requires that the printing heads can deliver defined amounts of liquid in the order of magnitude of 1000 pl or less in a reproducible manner. In this connection it is necessary that the volume can be kept constant between successive printing processes and this also applies to the speed with which the drops hit the analytical region. If the said parameters are kept constant, it can be ensured that the shape and size of the individual test spots is always the same and thus a regular pattern is obtained. These requirements can for example be met by a printer of the type ADK-201b from the Microdrop Company in Hamburg and a suitable electrical control (MD-E-201 from the same company). Another suitable printing head control is also described in EP-A-0 268 237. The printing heads which are parts of a production system are advantageously adjusted such that they deliver the same amount of liquid at the same speed. This also usually results in the same size of test spots for different printing liquids. If the viscosities or surface tensions of the individual printing liquids are very different it may be necessary to experimentally adjust the control of the printing heads such that test spots of equal size are obtained for different printing liquids.

In the production system the printing heads are firmly positioned and are not moved. It has turned out that this is of major importance for the accuracy and reproducibility of the production process. It has proven to be much more reliable to re-position a support to be printed under each of the printing heads rather than to move and thus to position the printing heads over the support. Although the printing heads of the production system according to the invention are not moved in order to deliver a drop of liquid, each of the printing heads can be adjusted to enable a correction of the lateral printing head position if it turns out that the test spots that are produced by a particular printing head deviate too strongly from the specified pattern.

Such an adjustment of the printing heads is carried out by a quality assurance device which is an optional component of the production system. A quality assurance device optically examines the multiple test elements and checks whether the test spots of an analytical region deviate from a specified pattern. Deviations from this pattern are converted into signals which carry out an adjustment of one or several printing heads. The optical examination of the test elements can be carried out by CCD cameras which monitor the maintenance of a specified pattern by means of image processing software. It is also possible to use printing liquids which contain one or several fluorescent dyes and to determine the position of the test spots by means of a fluorescence microscope or a fluorescence scanner.

It has proven to be advantageous for the production of multiple test elements according to the invention to adhere to certain process parameters for the printing. The fluid drops which emerge from the printing heads should have a speed of less than 5 m/s, preferably less than 2 m/s. It has been shown that these speeds are optimal for the production of uniform test spots and for avoiding splashing of the drop on the analytical surface. With the said speeds of the fluid drops it is advantageous to reduce the distance between the printing head nozzles and the analytical region to below 2 mm or even better below 500 $\mu$m in order to make the printing process as independent as possible from interferences of the path of the drop during flight and to be able to use low flight speeds. The volume of the individual fluid drops which are applied to the analytical region is preferably less than 1000 pl in order to produce sufficiently small test spots. In addition it is advantageous when the analytical region is hydrophobic in order to avoid bleeding of the applied drops. The surface is preferably made in such a way that a critical angle of more than 70° and even better of more than 80° is obtained with a 20 mM potassium phosphate solution.

Due to the very small amounts of liquid that are used in the printing process, drying is very rapid under normal room conditions. However, this fact which at first appears to be favourable, has proven to be disadvantageous when immunological test elements are produced. It has turned out that the relatively large antigen or antibody molecules require an adequate time in order to align themselves in a suitable manner on the surface of the support. This is especially the case when an analytical region is used which is coated with an antigen or antibody and the printing liquid contains a corresponding binding partner to which the reagent (usually also an antigen or antibody) is bound. This embodiment of the invention has the advantage that the binding partner and thus also the reagent can be firmly bound to the surface. In order to allow an adequate period for alignment of the binding partner molecules, the printing process is preferably carried out in an environment with an elevated relative air humidity, preferably 80%–98%. The air humidity is controlled by sealing off the entire production system or parts of the system to the environment by means of a housing and setting a specified air humidity within this housing by deliberate evaporation or condensation of water.

A production system according to the invention additionally has one or several positioning units for each holding unit which laterally displace and position the respective holding unit. A support is positioned and held within the holding unit as described above. The positions within the analytical region on which a fluid drop is to be applied are selected by means of the positioning unit. For this the positioning unit is steered by a control unit such that the holding unit is moved laterally to a certain position. The positioning unit can for example contain threaded rods which move in threaded holes in the holding unit and are driven by stepping motors which in turn are controlled by the control unit.

Multiple test elements according to the invention can each contain one or several test spots of a particular reagent. The latter is advantageous to ensure the entire test element does not become useless if there is a failure of a single test spot. On the other hand it is advantageous to have several test spots of one type in order to be able to average the analytical results that are obtained which compensates for errors when carrying out the analysis or for manufacturing variations of the test spots.

If a multiple test element has several test spots of the same type, then these are preferably applied onto the test element by one and the same printing head. For this the support is inserted and positioned in a holding unit, the holding unit is moved into a first position by its positioning unit and a fluid drop is released by the respective printing head. Subsequently the holding unit is moved into a further position of the specified pattern and an additional fluid drop is delivered. The method used in this process in which a single drop or a few drops are released in a time interval after selective control of the printing head is referred to as drop on demand.

As already described above, an essential characteristic of the present production system is that it has several holding units into which one and the same support is successively inserted and printed with liquid drops. Therefore the support is transported with the transport unit into different holding units in order to produce a multiple test element.

A robotic arm is for example suitable as a transport unit which grips a fresh support, inserts it in a first holding unit, removes it after the printing process and inserts it into a second holding unit etc.. However, it has proven to be more advantageous to use a transport unit which comprises a transport device for a lateral transport as well as a lifting device for the vertical transport of the supports. The transport device is preferably a conveyer belt which runs below the holding units. Furthermore it is preferable not to use a common conveyer belt with a planar transport belt but rather a conveyer belt on which there are holders to hold supports. Holders are for example possible which are permanently connected to the conveyer belt. In addition holders can be used which have pins etc. on their underside which engage in corresponding recesses of the conveyer belt. The said holders preferably have a socket shape on which the supports are placed. If supports are used with cross-pieces on the underside, it is advantageous when these cross-pieces are then situated on the sides of the holder and thus prevent the support from sliding off the holders. The lifting device of the transport unit lifts the support from the conveyer belt into the holding unit. The production system preferably has one lifting device for each holding unit. Such a lifting device can for example be a push rod which is moved vertically upwards by means of a motor from a first position in which it is located below the support in the process of which it grips under the support and, together with the support, moves into a second position in which the support is pressed against the vertical stop of the holding unit. Hence it is possible to design the lifting device so simply that only one movement in a direction in space has to be carried out. In this connection it is advantageous when two opposite sides of the support protrude over the holder on which it is located. In such an arrangement the lifting device can be moved directly to the support from the underside.

A control unit controls the movement of the transport unit, the holding and positioning of the supports in the holding units, the movement of the positioning units as well as the release of liquid from the printing heads. A conventional microprocessor can for example be used as a control unit which is equipped with suitable interface cards. The control unit regulates the process for producing diagnostic multiple test elements based on a stored programme. Such a production process which is also a subject matter of this invention comprises the following steps:

Positioning a support in a first holding unit below a first printing head,

Moving the first holding unit and the support positioned therein with a positioning unit into a position in which a first site of the analytical region is positioned below the first printing head, Release of one or several liquid drops from the first printing head onto the first site of the analytical region, Positioning the support in a second holding unit below a second printing head, Moving the second holding unit and the support positioned therein with a positioning unit into a position in which a second site of the analytical region is positioned below the second printing head, Release of one or several liquid drops from the second printing head onto the second site of the analytical region, wherein the support is moved into one or several additional positions while it is located in a holding unit in which drops of liquid are released to generate a specified pattern of test spots in the analytical region.

The process described above is so exact that a pattern of test spots can be generated in which the centres of the test spots deviate by less than 40 μm from the specified pattern.

The control unit described above also controls the holding units in order to hold and position the supports in the holding units. Furthermore the control unit controls the transport unit in order to supply the holding units with supports in a suitable time sequence.

The present invention also concerns an analytical method using multiple test elements according to the invention comprising the steps:

applying a sample liquid to the analytical region of a multiple test element, recording an image of the analytical region with the pattern of test spots arranged therein, evaluating the regions of the image in which test spots are located, determining the presence and/or the concentration of one or several analytes.

When test spots are used which change colour with an analyte, the multiple test element can be evaluated by a simple optical examination for example with a microscope or a CCD camera. However, according to the invention it is preferable to carry out analytical tests in which a fluorescent signal is formed or disappears when the test spots react with analytes. Such an analytical method can for example be carried out with a sandwich assay in which an antigen is located in a test spot which can be used to detect an antibody which may be present in the sample liquid. The antigen of the test spot reacts with the antibody from the analyte and forms a complex to which an additional antigen can bind which is labelled with a fluorescent dye. The labelled antigen can for example be derived from a reagent to which the sample liquid has previously been added or it can also be derived from a part of the surface of the support where it has previously been applied similarly to a test spot. The fluorescence signal generated in such a sandwich assay can also be recorded with a CCD camera that is sensitive for the emitted fluorescent light. The analytical region of a multiple test element can also be examined in a fluorescent microscope (see EP-A-0 601 714) or with a fluorescent scanner (see WO 96/02824). Images are obtained with the described methods which can either be evaluated visually or with the aid of a microprocessor.

Figure 2:
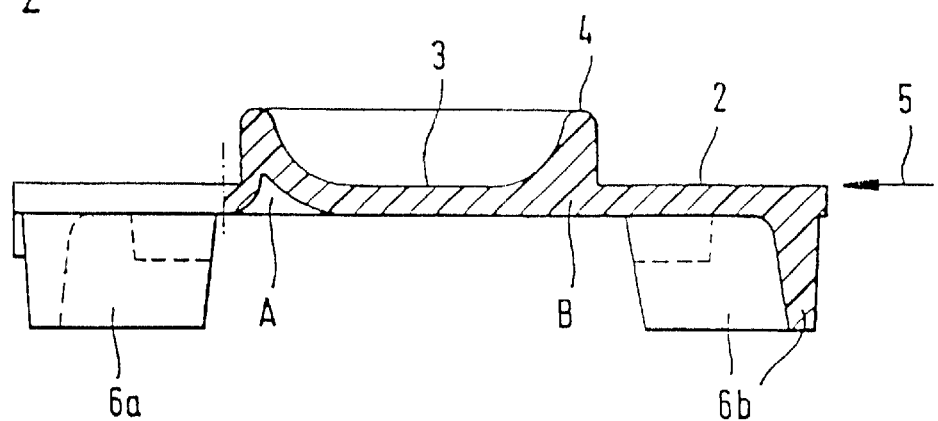
Figure 3:
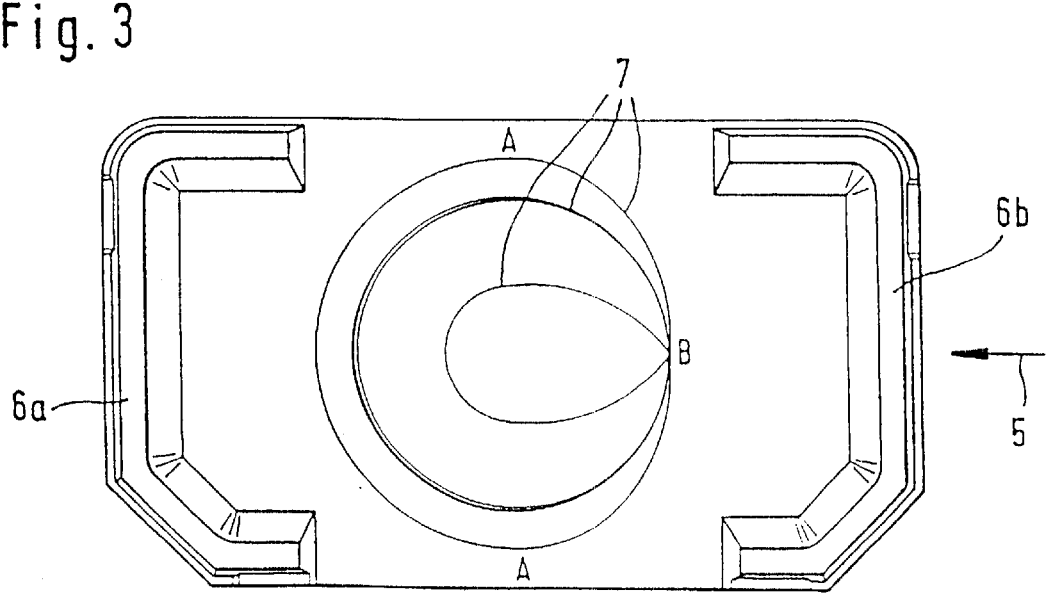
Figure 4:
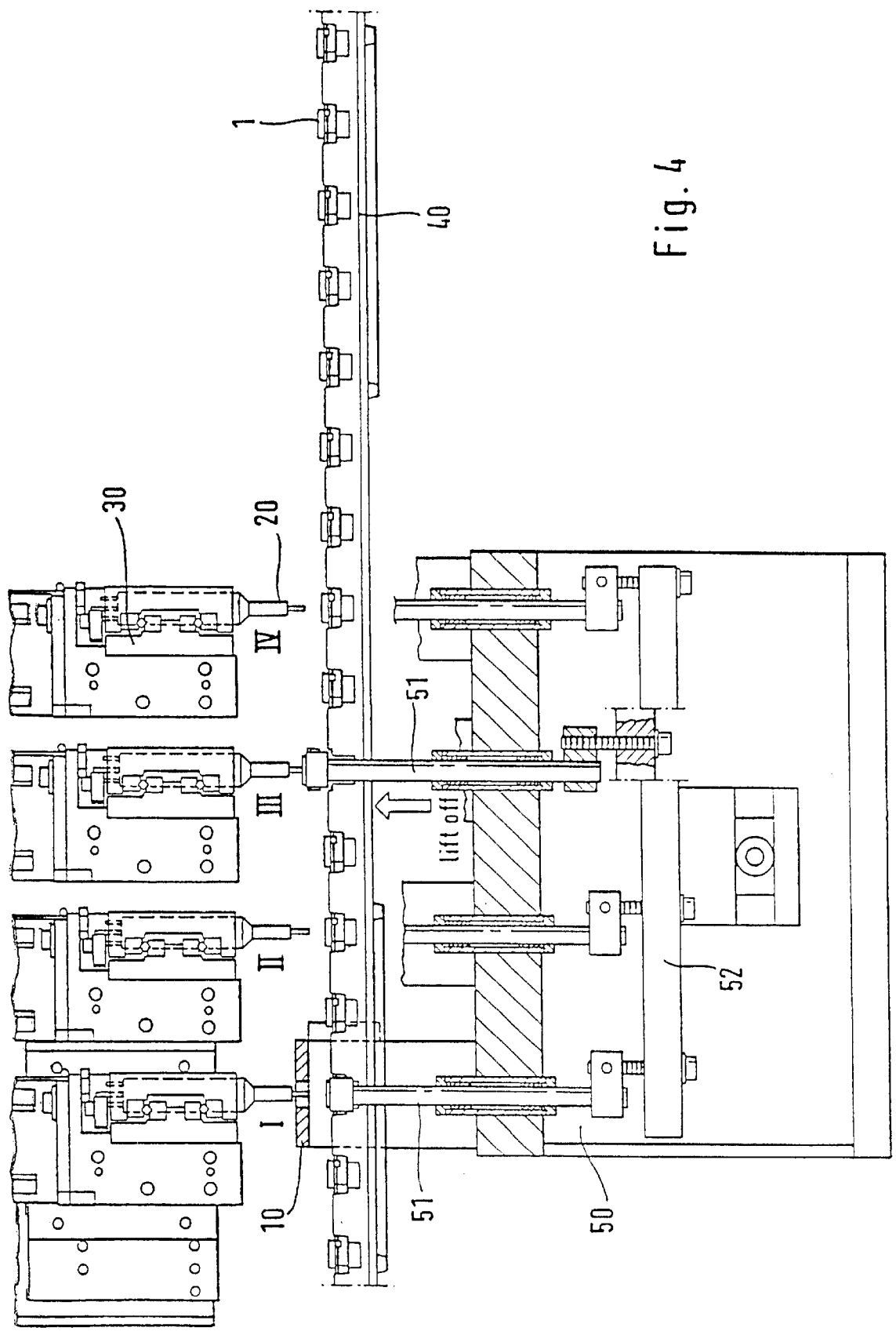
Figure 5:
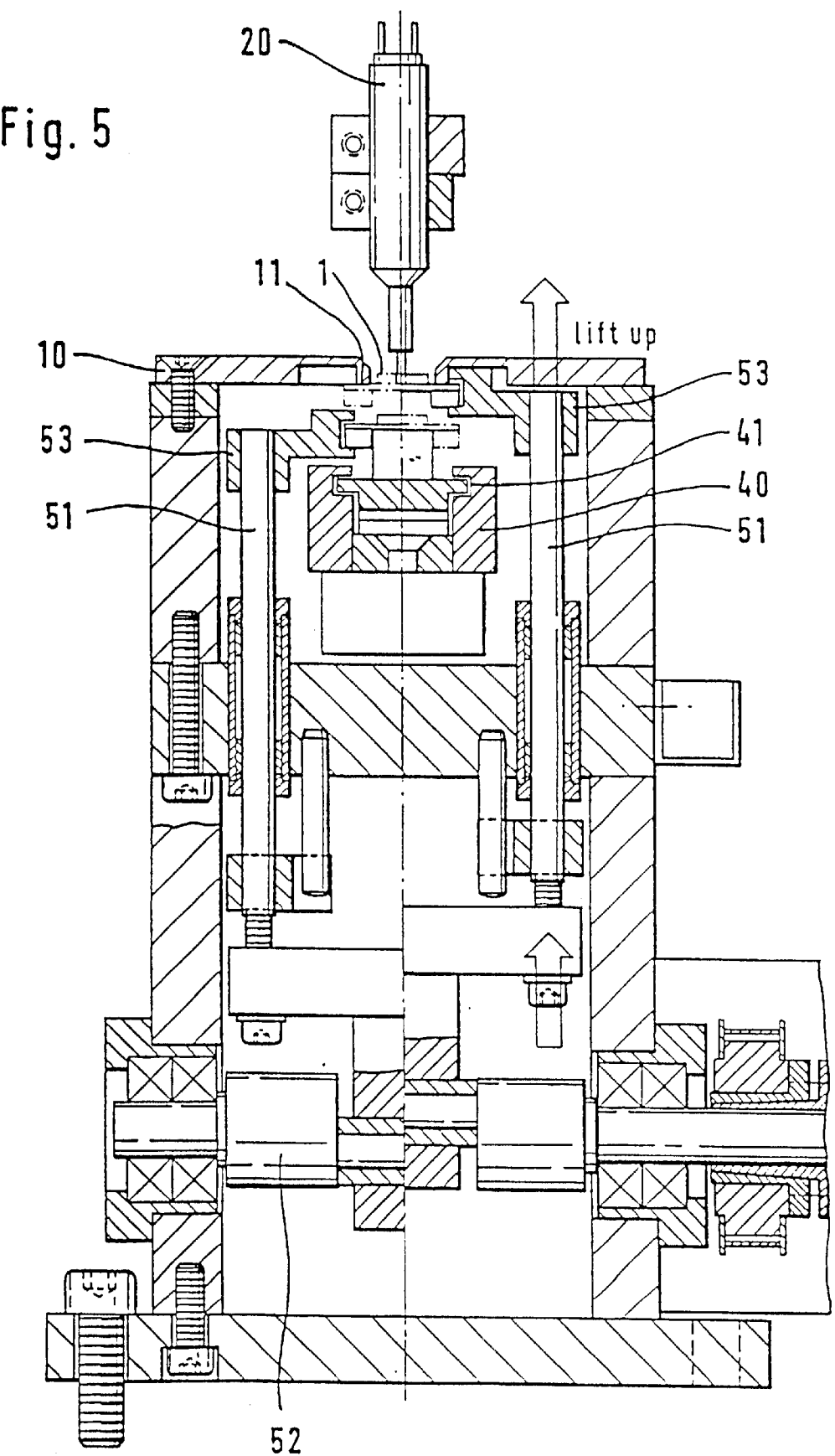
Figure 6:
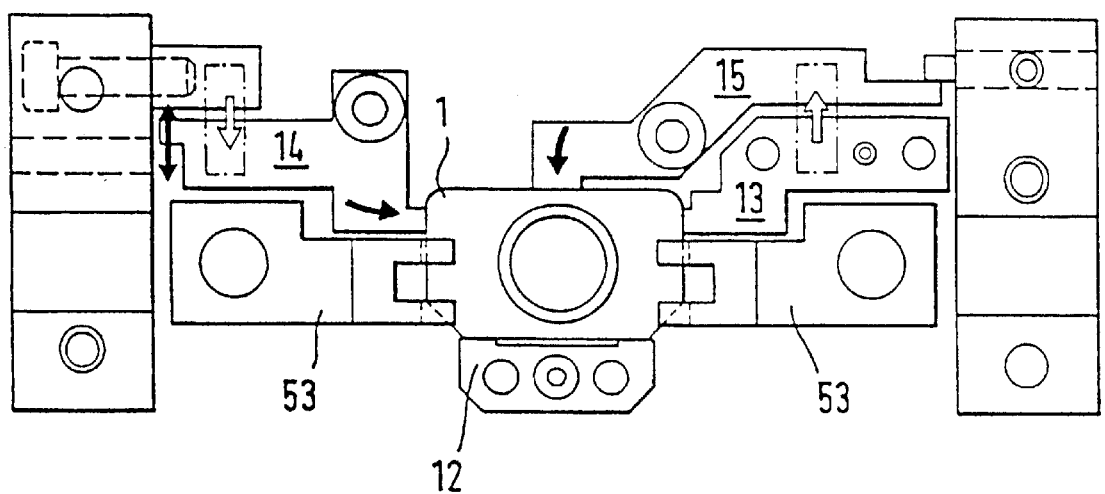
Figure 7:
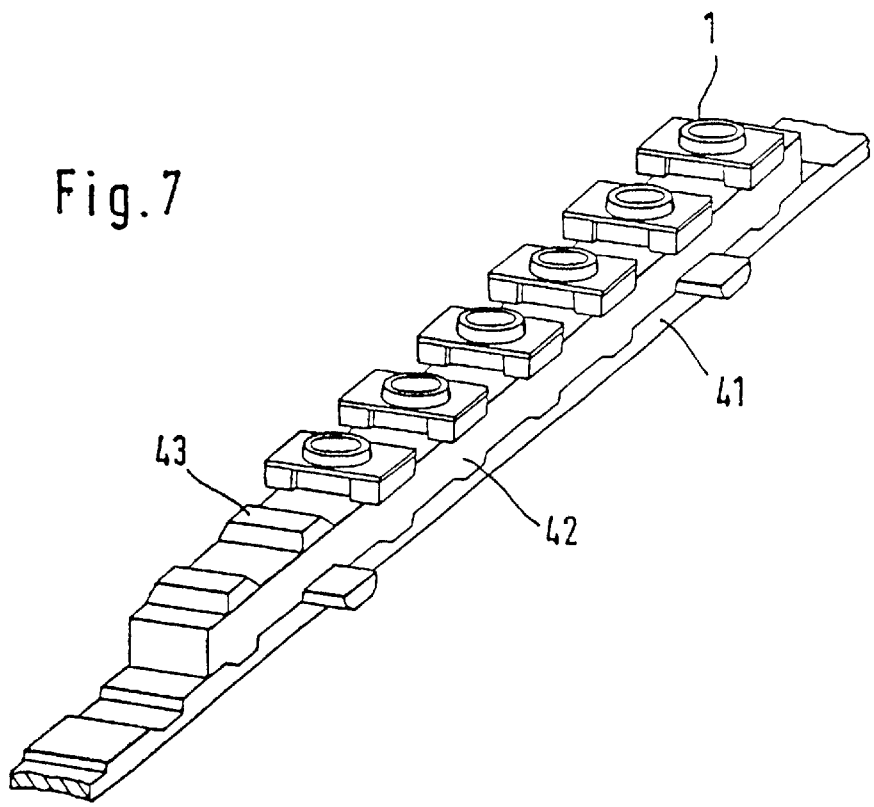
Figure 8:
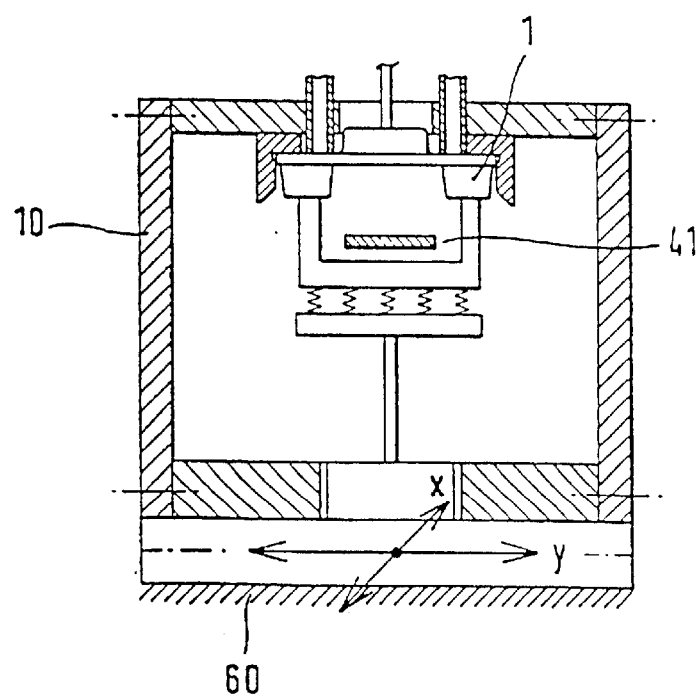
Figure 9:
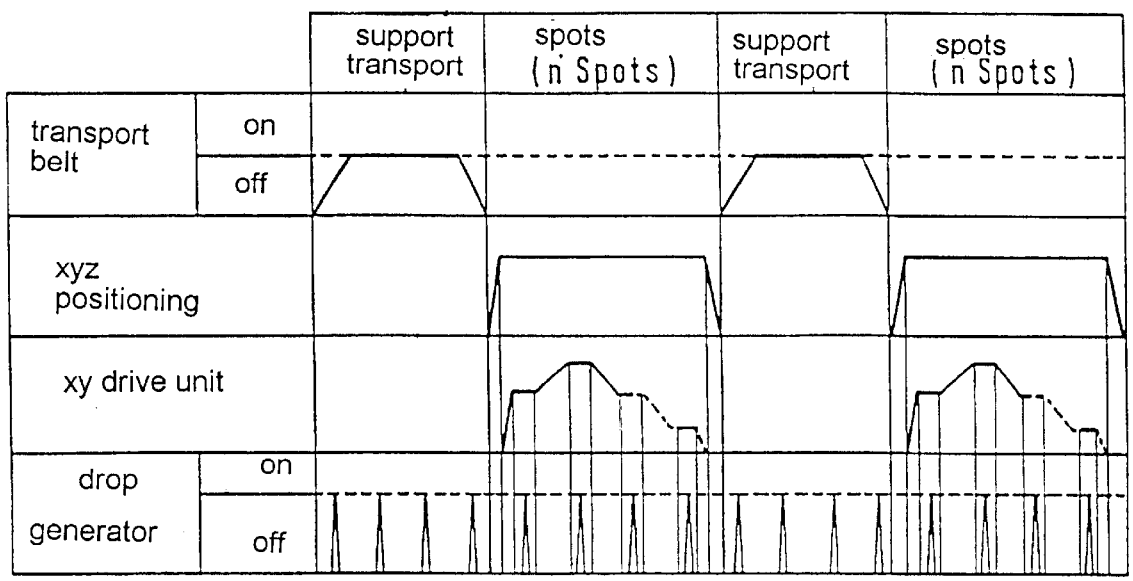
Figure 10:
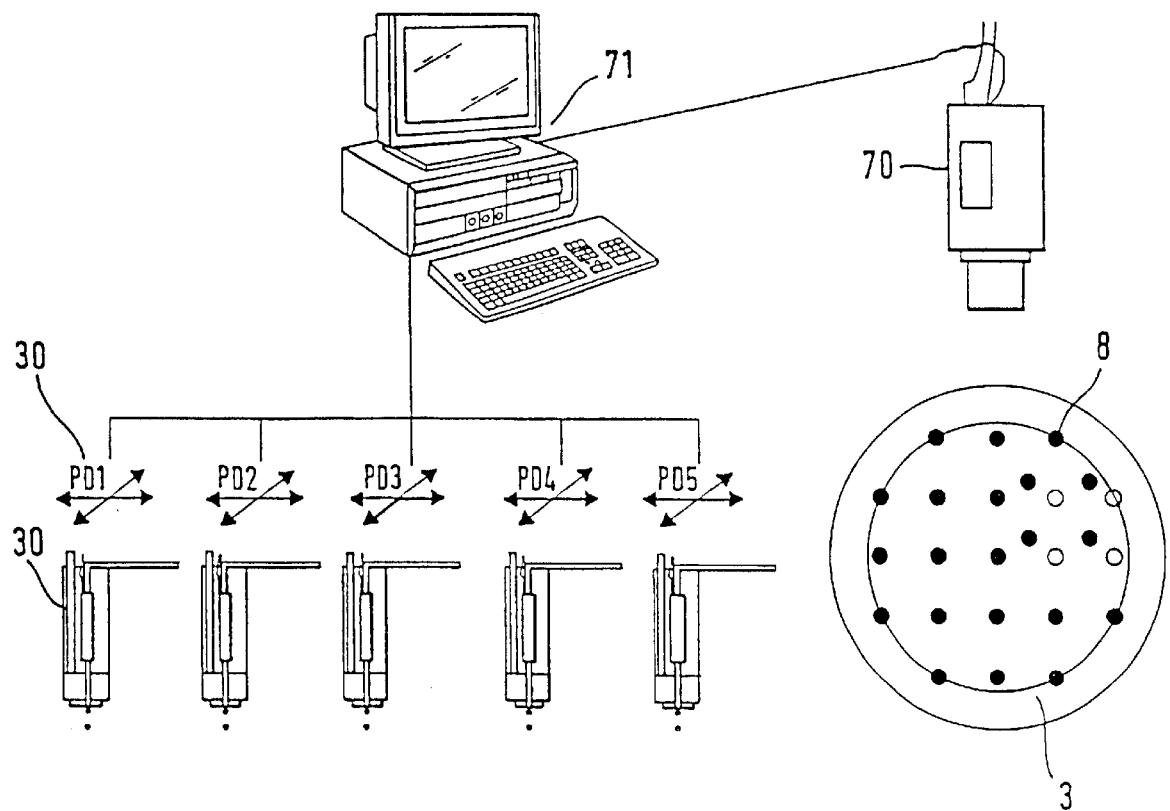
Figure 11:
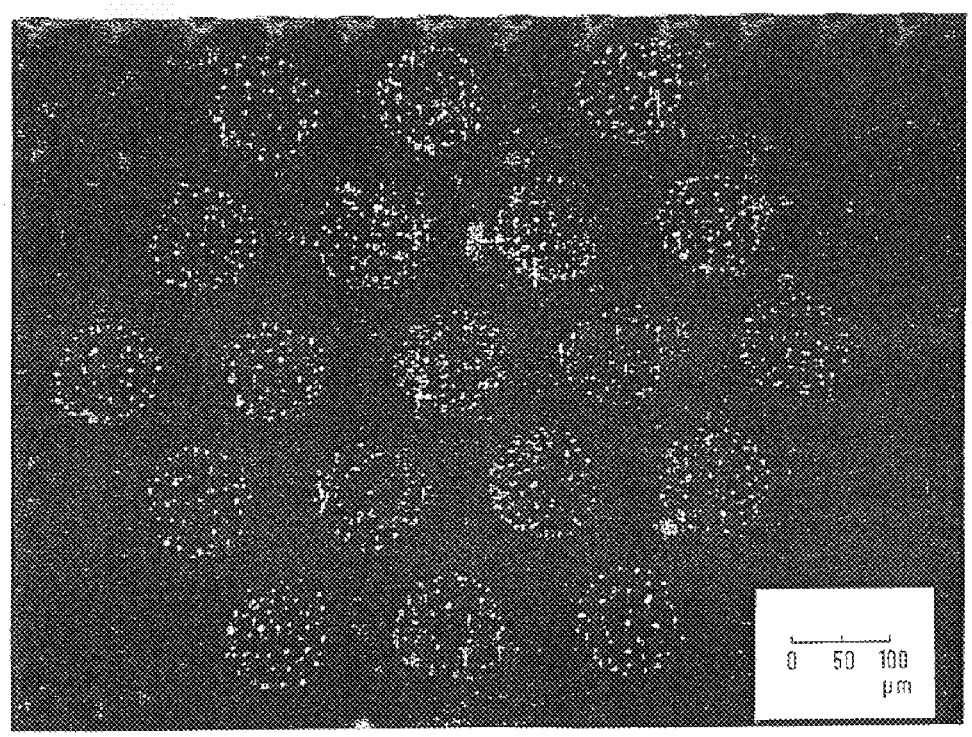
Figure 12:
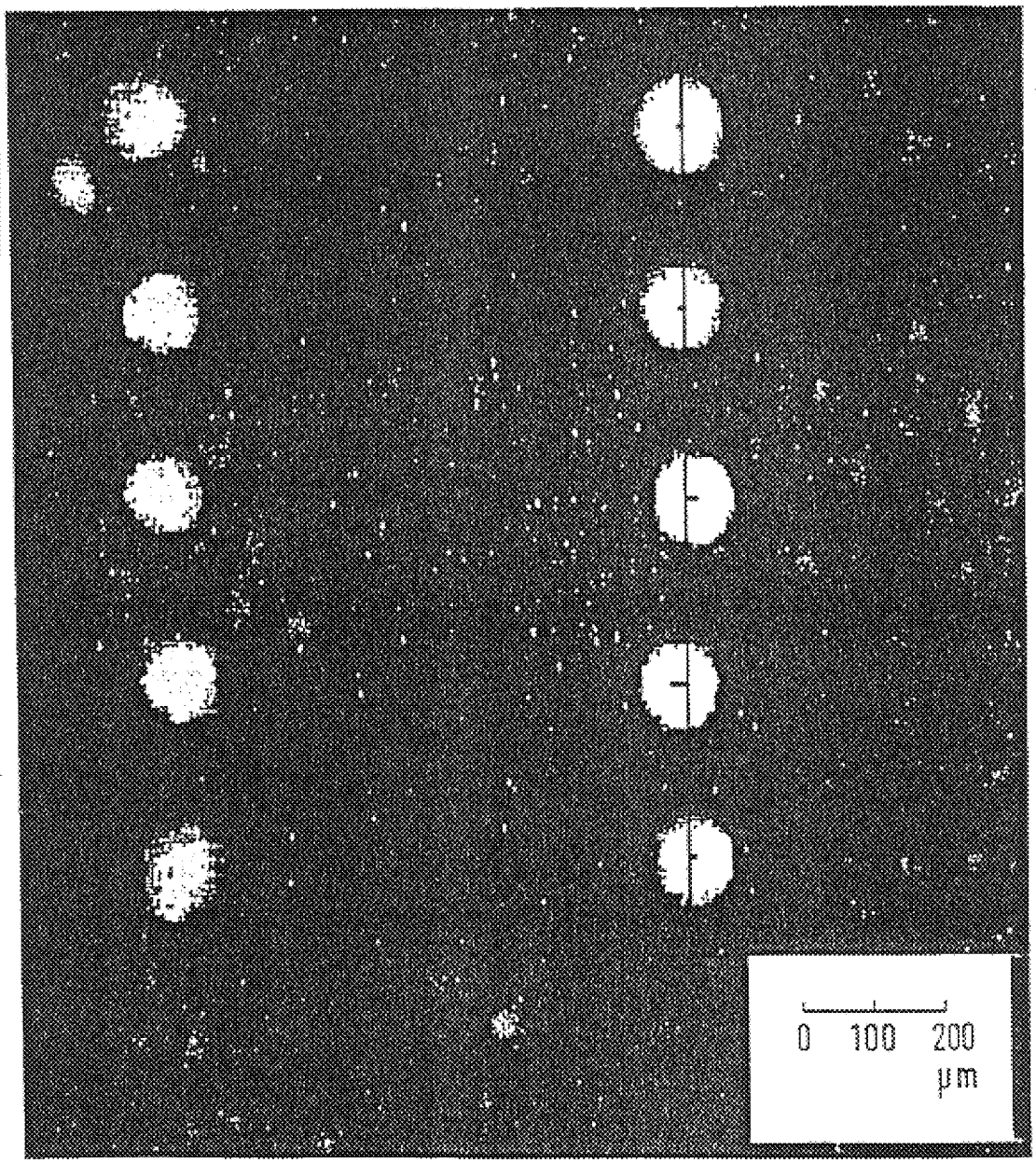

The present invention is further elucidated by some figures:

FIG. 1: top-view of a support
FIG. 2: cross-section through a support
FIG. 3: view of the support from the underside
FIG. 4: longitudinal section through a production system
FIG. 5: cross-section through a production system
FIG. 6: top-view of a holding unit
FIG. 7: transport belt with holders
FIG. 8: cross-section through a positioning unit
FIG. 9: flow diagram
FIG. 10: quality assurance unit
FIG. 11: enlarged view of a TSH test
FIG. 12: enlarged view of an analytical region with 10 different test spots.

A top-view of a support (1) for the production of multiple test elements is shown in FIG. 1. The support (1) has a basal surface (2) on which an analytical region (3) is located which is surrounded by a rim (4). The analytical region (3) and rim (4) together form a well into which liquid can be added. FIG. 1 also shows that two edges of the basal surface (2) are bevelled. This measure ensures an unequivocal orientation of the support during the production of a test element and when it is used later in an analytical method. FIG. 1 additionally shows the X and Y axis of a Cartesian coordinate system which define a plane which is parallel to the basal surface (2). Movement of the support in the XY plane is referred to as a lateral movement in this application. FIG. 1 is an approximately two-fold enlargement of an experimentally tested support.

FIG. 2 shows the support of FIG. 1 along the Y axis. FIG. 2 is an approximately 5-fold enlargement of a tested support. It can be seen that the planar analytical region (3) extends over a curve in the rim (4). Such a design of the well has proven to be advantageous for avoiding carry-over between successive analytical steps when using the test element. The shape is also advantageous for mixing liquids in the well by shaking or moving the support in the form of Lissajous figures without spilling or splashing.

FIG. 2 also shows the regions A and B which differ from one another although they are arranged symmetrically to the X axis (see FIG. 1). The chosen design in which the region A is free of plastic material below one side of the curve whereas region B is filled on the other side has a technical advantage for the injection moulding. In a preferred manufacturing process for the support, injection moulds are used which are parted on the upper side of the basal surface (2). The injection moulding material is injected from the side and on the level which is shown by the arrow (5). This procedure in conjunction with the described design of the regions A and B enables achievement of a particularly good quality of the analytical region (3) which is characterized by a very high planarity and few defects.

FIG. 2 also shows cross-pieces on the underside of the support. The view of the cross-piece (6a) is displaced in FIG. 2 to show a side-view of the support in this region. In contrast the cross-piece (6b) is shown as a section along the Y axis. It can be seen that cross-piece (6b) has a region on the side of the support as well as a region on the rear side of the support. Hence together with the diagram of the cross-piece (6a) it can be seen that the support has two cross-pieces which have a U-shape. However, the stop edges for lateral positioning can also be achieved by several cross-pieces which do not directly merge into one another as is the case for U-shaped cross-pieces. However, in order to provide a support which can be stored in a suitable manner the cross-pieces should have a recess in the X direction below the well. Such supports can be stacked and separated by movement in the X direction.

FIG. 3 shows a view of the support from the underside. The U-shaped cross-pieces can be seen in this diagram whose shape deviates slightly from the ideal U-shape due to the bevelling of the support. FIG. 3 also shows elevations (7) in the material on the underside of the basal surface (2). The elevations in the material are more or less circular and meet at point B which corresponds to region B of FIG. 2. The elevations (7) in the material are a result of corresponding grooves in the injection moulding tool. Such a design of the injection moulding tool has proven to be advantageous in order to control the flow of the injection moulding material such that an extremely planar and homogeneous analytical region is obtained. A combined view of FIGS. 2 and 3 shows that the region A which is not filled with injection moulding material covers most of the rim (4) and changes over continuously into the filled region B.

FIG. 4 shows a longitudinal section through a production system according to the invention. The four successive stations for coating supports are labelled with roman numerals. A holding unit (10) is shown schematically for station 1. FIG. 4 also shows the printing heads (20) allocated to the stations. Each of the printing heads is held in a fixed position and is not moved during the printing process. In addition each of the printing heads is located in an adjusting device (30) which can carry out an adjustment if it should turn out that the test spots applied by the respective printing head deviate from the specified pattern. The construction of such adjusting devices is sufficiently known in the prior art and is therefore not further elucidated here.

FIG. 4 shows in particular the operating principle of a preferred transport unit of the invention. The transport unit that is shown has a transport device (40) and a lifting device (50). The transport device (40) is composed of a transport belt on which the supports (1) are located and are transported in the longitudinal direction of the transport belt i.e. from station I towards station IV. The transport is intermittent such that in successive phases supports are respectively positioned below the printing heads. From this position the supports are lifted by the lifting device (50) from the transport belt and are positioned under a printing head. For this the lifting device has push rods (51) which can be moved by means of an eccentric drive (52). The resting position of the push rod (51) is shown for station I. The activated position in which the support is pressed is shown for station III as an example.

FIG. 5 shows a cross-section through a production system for multiple test elements. FIG. 5 is divided by the dashed vertical axis and the right and left parts are shown at different times. In the left half of FIG. 5 the push rod (51) is shown in its resting position. The upper side of the push rod carries a gripping device (53) which loosely surrounds a support (1). If the push rod (51) is lifted by the eccentric drive (52), the gripping device (53) grips under the support and guides it into the positioning unit (10). The holding unit (10) is only shown schematically in FIG. 5. It can, however, be seen that the holding unit (10) has vertical stop faces (11) against which the upper side of the basal surface of the support is pressed by the gripping device (53). An exact relative movement of the printing head and holding unit and an exact vertical positioning of the support in the holding unit enables the distance between the support or the analytical region of the support and the printing head to be very precisely adjusted. This is necessary if particularly small distances between the printing head and analytical region are required since positioning inaccuracies would lead to a crash between the printing head nozzle and the analytical region.

FIG. 5 also shows a cross-section of the transport device (40). The holders (41) on which the supports are located are held laterally by U-shaped guide rails to prevent tipping.

FIG. 6 shows a top-view of a holding unit for supports. The support (1) located in the holding unit is pressed from the underside by the gripping device (53) against a vertical stop (not shown). This has already been elucidated in connection with FIG. 5. The support is additionally pressed against an X stop (12) and a Y stop (13) in the holding unit. This is achieved by a first lever (14) which presses the support against the opposite Y stop (13) and by a second lever (15) which presses the support against the X stop (12). The first and second lever are each pivoted around an axis and are rotated by the push rods in the directions shown by the white open arrows. The holding unit shown enables an extremely exact positioning of the support in the three directions in space which is achieved by a suitable interaction of cross-pieces on the supports and positioning devices on the holder. With regard to the cross-pieces on the support it is of particular importance that in each case cross-pieces or parts of cross-pieces are located on opposing sides of the support so that when pressure is applied to a cross-piece with a lever the support is positioned on the opposite cross-piece.

FIG. 7 shows a transport belt which is part of a transport device. The transport belt (41) is flexible so that it can be guided over guide rollers. A holder unit on which several supports can be transported is located on the transport belt. The holding unit (42) shown has eight sockets (43) which protrude above the holder unit and match the shape of the supports so that the supports are held by the sockets. The holder unit (42) is preferably designed such that the supports protrude laterally when they are located on the sockets. This allows the supports to be lifted in a simple manner and transported into the holding unit as described in connection with FIGS. 4 and 5.

FIG. 8 shows a schematic cross-section through a positioning unit. The positioning unit comprises a base plate (60) which is permanently fixed. The holding unit (10) is laterally moved relative to this base plate. The holding unit is only shown schematically in FIG. 8. In addition in FIG. 8 the direction in which the holding unit is moved is only indicated by arrows in the X and Y direction. Devices for the exact movement and positioning in the X and Y direction are adequately known in the prior art and are therefore not further elucidated here.

FIG. 9 shows a flow diagram which shows the chronological coordination of the individual components of the production system. Firstly the transport belt is switched on and the support is positioned under a first printing head (referred to as support transport). In a second step the support is positioned in the holding unit and positioned with the positioning unit (referred to as XY transport unit) in such a way that defined sites of the support are arranged below the printing head. As soon as a site has been positioned below the printing head a drop of printing liquid is released onto the support (the printing head is referred to as a drop generator in FIG. 9). Following this step the support is positioned under a new printing head and here one or several printing processes are carried out again as described above.

FIG. 10 shows a quality assurance unit which is used to adjust the printing heads. The analytical region (3) of a support is shown greatly enlarged in the figure. It can be seen that some of the applied test spots (8) are outside of the specified positions (bright circles) of the pattern. The analytical region of the test element is recorded with a CCD camera (70) and the information obtained is transmitted to a computer (71). The computer analyses the image, recognizes the points which deviate from the pattern, allocates them to a printing head which has caused them and steers this printing head so as to avoid a deviation from the pattern in later test elements.

The production of multiple test elements according to the invention is further elucidated in the following by examples:

EXAMPLE 1

A support according to FIGS. 1–3 was printed with test spots using an apparatus according to FIGS. 4–6. Before the printing process the analytical region of the support was uniformly coated with an antibody against IgG such that the unevenness of the surface obtained is less than 10 $\mu$M and the contact angle with reference to a 20 mM potassium phosphate solution is 90°. The support was subsequently printed with a printing liquid in which a monoclonal antibody against the thyroid stimulating hormone (TSH) was present which is an IgG. A solution of 1.0 mg/ml of the antibody was diluted with 20 mM potassium phosphate solution until a pH of 7.4 was adjusted and the solution obtained was filtered with a filter of 0.02 $\mu$m pore size. Afterwards the solution was degassed by shaking for 10 min at 35° C. and 200–300 mbar vacuum.

The printing solution obtained was printed onto the analytical region of the test element using a printing head ADK-201b from the Microdrop Company (Hamburg). At first a pressure was applied in the reservoir of the printing liquid which was 20 mbar below the ambient pressure and the printing head was operated with a voltage of 68 V at a frequency of 0.5 Hz and an impulse width of 115 ms. The size of the droplets obtained by this was 55 $\mu$m during flight and the size of the test spots achieved with this was 95 $\mu$m in diameter.

After the printing process the support was incubated for 20 seconds and then rinsed with the following solutions:

20 mM potassium phosphate solution at pH 7.7
0.9% sodium chloride
2% sucrose
0.01% sodium azide
1% bovine serum albumin In order to carry out an analysis for TSH, 50 $\mu$l sample containing TSH was added to the well of the test element and incubated for 10 minutes. Subsequently the sample was removed by washing and then 50 $\mu$l of a conjugate composed of an antibody against TSH and an antibody against digoxin was added and incubated for 10 minutes. After washing again 50 $\mu$l of a conjugate of digoxin bound to microparticles was added in which a fluorescent dye was present. After a further wash process, the test element was recorded with a fluorescence microscope which led to FIG. 11.

FIG. 11 shows a greatly enlarged view of an analytical region containing 19 test spots. The enlargement of the pattern shown is about 200-fold and the strict regular arrangement of the individual test spots can be seen. Each of the test spots has a granular form which is due to individual fluorescent microparticles that have accumulated fluorescent dye. Despite the statistical distribution of the microparticles over the test spots it can be seen that the individual test spots have a clearly contoured shape and are arranged very regularly in the specified pattern.

EXAMPLE 2

In an additional experiment a support was printed with 10 different antibodies. For this a support was again used whose analytical surface was coated with an IgG antibody and to which antibodies against various analytes were bound. In contrast to example 1 antibodies were used for the detection which were labelled with resorufin which can be detected directly with a fluorescent photometer. FIG. 12 shows the image of an analytical region which was obtained with a fluorescent photometer based on the fluorescence obtained with resorufin. The following antibodies were located in the left row of FIG. 12 from top to bottom:

a mixture of various antibodies against hepatitis C virus
   antibody against NCV-NS4/3
   antibody against HCV helicase
   antibody against HCV core
   antibody against HB core
in the right row from top to bottom:
   antibody against HIV/P24
   antibody against HIV/GP41P1
   antibody against HIV/GP41P2
   antibody against HIV mix
   antibody against HBsAG FIG. 12 shows that despite printing the test support with 10 different printing heads it was possible to achieve a very accurate arrangement. In order to illustrate this, a trend line was drawn through the right row of test spots and the deviation of the test spots from this trend line was determined by linking the centres of the respective test element by the shortest path with the trend line. The length of these connecting lines directly yields the deviation of the test spots from the specified pattern. The test spot which was second from the bottom had the greatest deviation from the pattern. However, the deviation is less than 25 $\mu$m.

List of Reference Numerals (1) support
(2) basal surface
(3) analytical region
(4) rim
(5) injection direction
(6) cross-pieces
(7) material elevations
(8) test spot
(10) holding unit
(11) vertical stop face
(12) X stop
(13) Y stop
(14) first lever
(15) second lever
(20) printing head
(30) adjusting device
(40) transport device
(41) transport belt
(42) holder unit
(43) socket
(50) lifting device
(51) push rod
(52) eccentric drive
(53) gripper
(60) base plate
(70) ccD camera
(71) computer

What is claimed is:

1. A system for producing multiple diagnostic test elements, comprising:
   a) a support with an analytical region for applying diagnostic test spots;
   b) a first holding unit into which the support can be inserted and positioned;
   c) a first printing head which is arranged above the first holding unit and which can be used to release fluid drops of a first reagent onto the analytical region of the support;

d) a first positioning unit which can laterally displace and position the first holding unit;

e) a second holding unit into which the support can be inserted and positioned;

f) a second printing head which is arranged above the second holding unit and which can be used to release fluid drops of a second reagent onto the analytical region of the support;

g) a second positioning unit which can laterally displace and position the second holding unit;

h) a transport unit which can transport the support into the holding units;

i) a control unit which controls the transport unit, the holding units and the positioning units and the release of reagent from the printing heads; and j) at least one quality assurance device which can optically examine the fluid drops of the first or second reagent and convert deviations of the fluid drops from a specified pattern into signals which control a lateral adjustment of a relative position of the first printing head with respect to the first holding unit or of a relative position of the second printing head with respect to the second holding unit.

2. The system of claim 1 wherein the printing heads are not moved laterally in order to release the fluids onto the support.

3. The system of claim 1 wherein at least part of the system is closed from the environment by a housing in which a specified air humidity can be adjusted.

4. The system of claim 1 wherein the holding units can be loaded with supports from below.

5. The system of claim 4 wherein the holding units have stop elements against which the support can be pressed from below and vertically positioned.

6. The system of claim 1 wherein the control unit can control coordinated movements of the holding units and the release of fluid from the printing heads in such a way that the specified pattern of test spots can be applied to the analytical region of a test element.

7. The system of claim 6, wherein the individual test spots deviate from the specified pattern by less than 40 μm.

8. The system of claim 7 wherein the deviation from the pattern is less than 25 μm.

9. The system of claim 1 wherein the printing heads can be held in adjusting devices which enable a lateral adjustment of the printing heads.

10. The system of claim 9 wherein the at least one quality assurance device can control the adjustment of the printing head positions by means of the adjusting devices.

11. The system of claim 1 wherein the at least one quality assurance device comprises at least one CCD camera.

12. The system of claim 11 wherein at least one of the first and the second reagents contains one or several fluorescent dyes and the position of the test spots can be determined by a fluorescent scanner.

13. The system of claim 1 wherein the transport unit comprises a conveyer device and a lifting device.

14. The system of claim 13 wherein the lifting device can grip the underside of the support and lift the support into the holding unit.

15. The system of claim 13 wherein the conveyer device comprises a conveyer belt on which holders for holding supports are located.

16. The system of claim 15 wherein the supports have a basal surface on the underside of which one or several cross-pieces are located which rest against the sides of the holder when the supports are located on the holders and the cross-pieces can prevent the supports from sliding from the holders.

17. The system of claim 15 wherein the supports protrude over the holders on two opposite sides.

18. The system of claim 1 wherein the reagent drops emerging from the printing heads have a speed of less than about 5 meters per second, and the distance of the printing head nozzles from the analytical region is less than about 2 mm during the printing process.

19. The system of claim 18 wherein the reagent drops emerging from the printing heads have a speed of less than about 2 meters per second.

20. The system of claim 18 wherein the volume of an individual reagent drop is less than about 1000 pl.

21. The system of claim 18 wherein the distance of the printing head nozzles from the analytical region is less than about 500 μm during the printing process.

22. The system of claim 21 wherein the reagent drops emerging from the printing heads have a speed of less than about 2 meters per second.

23. A process for producing a multiple diagnostic test element in which a pattern of test spots is applied to a support, comprising the following steps:

a) positioning a support in a first holding unit below a first printing head, the support comprising an analytical region, b) moving the first holding unit and the support positioned therein with a positioning unit into a position in which a first site of the analytical region is positioned below the first printing head, c) releasing one or several reagent drops from the first printing head onto the first site of the analytical region, d) positioning the support in a second holding unit below a second printing head, e) moving the second holding unit and the support positioned therein with a positioning unit into a position in which a second site of the analytical region is positioned below the second printing head, and f) releasing at least one reagent drop from the second printing head onto the second site of the analytical region, g) wherein steps a) through c) and d) through f) are repeated with said printing heads or with other printing heads so that a specified pattern of test spots is generated in the analytical region; and h) optically examining the test spots and converting deviations from the specified pattern into signals which control a lateral adjustment of a relative position of one or more printing heads with respect to its corresponding holding unit.

24. The process of claim 23, wherein the centers of the test spots deviate by less than 40 μm from the specified pattern.

25. The process of claim 23 wherein the support is inserted from below into the holding units.

26. The process of claim 23 wherein when the test spots deviate from the specified pattern, the printing heads are adjusted by adjusting devices.

27. The process of claim 23 wherein the supports are moved between the holding units by a transport device.

28. The system of claim 1, wherein the at least one quality assurance device can examine all the fluid drops of reagent in the analytical region simultaneously.

29. The system of claim 1, wherein the at least one quality assurance device can examine each fluid drop of reagent as it is released onto the analytical region.

30. The process of claim 23, wherein step h) is performed after steps a) through c) and after steps d) through f).

31. The process of claim 23, wherein step h) is performed after step g).

\* \* \* \* \*

UNITED STATES PATENT AND TRADEMARK OFFICE
CERTIFICATE OF CORRECTION

PATENT NO. : 6,544,796 B1
DATED : April 8, 2003
INVENTOR(S) : Udo Eichenlaub et al.

It is certified that error appears in the above-identified patent and that said Letters Patent is hereby corrected as shown below:

Title page,
Item [30], Foreign Application Priority Data, delete "197 07 204" and substitute -- 197 07 204.6 -- in its place.

Item [56], References Cited, FOREIGN PATENT DOCUMENTS, insert the following:

-- DE    2729333C2    2/78
   DE    3346795A1    7/85 --.

Signed and Sealed this

Seventh Day of September, 2004

JON W. DUDAS
*Director of the United States Patent and Trademark Office*